(12) United States Patent
Li et al.

(10) Patent No.: US 12,339,269 B2
(45) Date of Patent: Jun. 24, 2025

(54) DEVICE FOR STRATIFIED IN-SITU MONITORING OF WATER QUALITY AND DISSOLVED OXYGEN OF SEDIMENTS IN TIDAL RIVER NETWORK REGION

(71) Applicant: South China Institute of Environmental Science, MEE (Ecological and Environmental Emergency Research Institute, MEE), Guangzhou (CN)

(72) Inventors: Weijie Li, Guangzhou (CN); Huaiyang Fang, Guangzhou (CN); Runmian Yang, Guangzhou (CN); Hongwei Du, Guangzhou (CN); Jiale Chen, Guangzhou (CN); Fantang Zeng, Guangzhou (CN)

(73) Assignee: SOUTH CHINA INSTITUTE OF ENVIRONMENTAL SCIENCE, MEE (ECOLOGICAL AND ENVIRONMENTAL EMERGENCY RESEARCH INSTITUTE, MEE), Guangzhou (CN)

( * ) Notice: Subject to any disclaimer, the term of this patent is extended or adjusted under 35 U.S.C. 154(b) by 316 days.

(21) Appl. No.: 18/181,333

(22) Filed: Mar. 9, 2023

(65) Prior Publication Data
US 2024/0201160 A1    Jun. 20, 2024

(30) Foreign Application Priority Data
Dec. 16, 2022    (CN) .......................... 202211622093.2

(51) Int. Cl.
*G01N 33/18*    (2006.01)
*G01N 1/10*    (2006.01)

(52) U.S. Cl.
CPC ........... *G01N 33/1886* (2013.01); *G01N 1/10* (2013.01); *G01N 2001/1031* (2013.01)

(58) Field of Classification Search
CPC ................. G01N 33/1886; G01N 1/10; G01N 2001/1031; G01N 33/18
See application file for complete search history.

(56) References Cited

U.S. PATENT DOCUMENTS

2018/0292208 A1* 10/2018 Moore ............... G01N 33/1886

FOREIGN PATENT DOCUMENTS

| CN | 107192801 A | * | 9/2017 | ............. G01N 33/18 |
| CN | 112505283 A | * | 3/2021 | ............. B63B 21/26 |

(Continued)

*Primary Examiner* — Laura Martin
*Assistant Examiner* — Anthony W Megna Fuentes
(74) *Attorney, Agent, or Firm* — Muncy, Geissler, Olds & Lowe, P.C.

(57) ABSTRACT

A device for stratified in-situ monitoring of the water quality and dissolved oxygen of sediments in a tidal river network region includes a floating platform. Three take-up and pay-off assemblies are fixedly connected to the edge of a top surface of the floating platform. The device can provide high-density data of stratified dissolved oxygen, all monitoring units perform sampling and monitoring directly at the positions where they are located, samples do not need to be transferred, sediments will not be disturbed, and monitoring is performed in the field environment, such that researchers can obtain the long-term diurnal change of stratified dissolved oxygen and the continuous change process of dissolved oxygen in one and even multiple hydrologic years, and basic data is provided for study of the dissolved oxygen change mechanism and accurate control of the water environment in tidal river network regions.

9 Claims, 8 Drawing Sheets

(56) References Cited

FOREIGN PATENT DOCUMENTS

| | | | | | |
|---|---|---|---|---|---|
| CN | 113030411 | A | * 6/2021 | ............. | G01D 21/02 |
| KR | 20200113599 | A | * 10/2020 | ............... | G01N 1/10 |

* cited by examiner

DEVICE FOR STRATIFIED IN-SITU MONITORING OF WATER QUALITY AND DISSOLVED OXYGEN OF SEDIMENTS IN TIDAL RIVER NETWORK REGION

BACKGROUND OF THE INVENTION

1. Technical Field

The invention relates to the technical field of environment monitoring, in particular to a device for stratified in-situ monitoring of the water quality and dissolved oxygen of sediments in a tidal river network region.

2. Description of Related Art

Dissolved oxygen is an important factor determining whether natural river water is polluted and an important indicator for evaluating whether natural river water has a self-cleaning capacity, and is indispensible for the survival of aquatic organisms in rivers. When the content of dissolved oxygen in water is too low, anaerobic bacteria will breed to cause anaerobic decomposition, which makes water black and odorous and releases poisonous gases such as methane and hydrogen sulfide, thus compromising the sensory effect of water and severely threatening the survival of aquatic organisms. The content of dissolved oxygen in water is closely related to the differential pressure of oxygen in air, and the temperature, salinity and the flow form of water. In addition, the stratified change of water caused by the tidal action of rivers also has an influence on the distribution of dissolved oxygen in water. In recent years, China has attached greater importance to water environment treatment, so the quality of surface water environments in China is improved steadily, and the proportion of water with high sectional quality increases stably. However, the content of dissolved oxygen on the cross-section of tidal river network regions in China is low, and under the condition that other performance indicators are up to standard, the unqualified dissolved oxygen will affect the proportion of high-quality water to some extent. Although some achievements have been obtained in the study of low dissolved oxygen in tidal river network regions both at home and abroad, the formation mechanism of low dissolved oxygen needs to be further studied.

At present, dissolved oxygen in water is measured mainly through various handheld dissolved oxygen meters. However, online monitoring equipment can only monitor dissolved oxygen in surface water. A self-recording dissolved oxygen meter has to be used to observe the stratified change of dissolved oxygen in river network regions. In order to observe oxygen consumption of sediments, the sediments have to be collected from water to the bank and then transferred to be tested, which leads to disturbance to the sediments and neglects the change of the field environment, so this method has limitations. In addition, existing online monitoring equipment is of an integrated structure, that is, various monitoring sensors are integrated and then placed in water. However, due to the fact that monitoring sensors with different functions should to be disposed at different positions in water, for example, sensors for monitoring dissolved oxygen of sediments and sensors for monitoring the water quality need to be disposed at different positions in water, it is difficult to ensure that all monitoring units with different functions of the existing online monitoring equipment can be disposed at suitable positions.

In view of this, a device for stratified in-situ monitoring of the water quality and dissolved oxygen of sediments in a tidal river network region is proposed to solve the above-mentioned problems.

BRIEF SUMMARY OF THE INVENTION

The objective of the invention is to provide a device for stratified in-situ monitoring of the water quality and dissolved oxygen of sediments in a tidal river network region to solve the problems mentioned in the description of related art.

To fulfill the above objective, the invention provides the following technical solution: a device for stratified in-situ monitoring of the water quality and dissolved oxygen of sediments in a tidal river network region comprises a floating platform, wherein three take-up and pay-off assemblies are fixedly connected to an edge of a top surface of the floating platform, each take-up and pay-off assembly comprises a sheave wheel, a first cable, a base plate, two oblique rods and a first gear motor, a water quality monitoring assembly, a sediment monitoring assembly and a first balancing weight are fixedly connected to bottom ends of the three first cables on the three take-up and pay-off assemblies respectively, and a central control unit is fixedly connected to the top surface of the floating platform;

The water quality monitoring assembly comprises a shell, a pressure sensor and a dissolved oxygen meter are fixedly connected to one side of the shell, two water quality samplers are fixedly connected to two sides of the shell respectively, top ends of the water quality samplers are open, two cover plates are rotatably connected to the two sides of the shell and are located above the two water quality samplers respectively, and the center of a top end of the shell is fixedly connected to a bottom end of the corresponding first cable;

The sediment monitoring assembly comprises a circular counterweight shell, a vertical opening is vertically formed in the circular counterweight shell, two horizontal support rods are fixedly connected to an inner wall of the vertical opening, a main plate is fixedly connected between the two horizontal support rods, a camera and a lamp are fixedly connected to one side of the main plate, a sliding groove is formed in a side, away from the camera, of the main plate, a sliding block is vertically and slidably connected into the sliding groove, a movable plate is fixedly connected to a side, located outside the sliding groove, of the sliding block, and a dissolved oxygen probe is fixedly connected to a bottom end of the movable plate.

Preferably, a cavity is formed in the shell, a double-shaft gear motor is fixedly connected into the cavity and is located between the two cover plates, two drive shafts are fixedly connected to two shaft ends of the double-shaft gear motor respectively, and ends of the two drive shafts are fixedly connected to shaft ends of the two cover plates.

Preferably, a counterweight frame is fixedly connected to a bottom surface of the shell, and a lithium battery is fixedly connected into the cavity.

Preferably, a lead screw is vertically and rotatably connected into the sliding groove, a threaded sleeve is vertically and fixedly connected into the sliding block, and the lead screw is threadedly connected to the threaded sleeve.

Preferably, a second gear motor is fixedly connected to an inner top surface of the main plate, a shaft end of the second gear motor is fixedly connected to an end of the lead screw, a top surface of the circular counterweight shell is fixedly connected to a support, and the support is fixedly connected to a bottom end of the corresponding first cable.

Preferably, three dissolved oxygen sensors are fixedly connected to the first cable fixedly connected to the first balancing weight, a second cable is fixedly connected to a bottom surface of the floating platform, and a second balancing weight is fixedly connected to a bottom end of the second cable.

Preferably, a power distribution box is fixedly connected to the top surface of the floating platform, three oblique frames are fixedly connected to the top surface of the floating platform and are located around the power distribution box, photovoltaic panels are fixedly connected to the oblique frames, an automatic meteorological station is fixedly connected to the top surface of the floating platform, and multiple fences are fixedly connected to the edge of the top surface of the floating platform.

Preferably, the base plates are fixedly connected to the edge of the top surface of the floating platform and are located between multiple fences, the two oblique rods are fixedly connected to a top surface of each base plate, the sheave wheel is rotatably connected between top ends of the two oblique rods, the first cable is wound on the sheave wheel, an end of the first cable is fixedly connected to the sheave wheel, the first gear motor is fixedly connected to one side of a top end of one of the two oblique rods, and a shaft end of the first gear motor is fixedly connected to an end of the sheave wheel.

Preferably, the central control unit comprises a shell fixedly connected to the top surface of the floating platform, a touch display screen is fixedly connected to a side wall of a top surface of the shell, a host computer and a transmission module are fixedly connected into the shell, and a terminal plate and a control panel are fixedly connected to a side wall of the shell.

Compared with the prior art, the invention has the following beneficial effects:

The device of the invention can provide high-density data of stratified dissolved oxygen, all monitoring units perform sampling and monitoring directly at the positions where they are located, samples do not need to be transferred, sediments will not be disturbed, and monitoring is performed in the field environment, such that researchers can obtain the long-term diurnal change of stratified dissolved oxygen and the continuous change process of dissolved oxygen in one and even multiple hydrologic years, and basic data is provided for study of the dissolved oxygen change mechanism and accurate control of the water environment in tidal river network regions; during the monitoring process, the monitoring units are separated from each other, and the positions of the monitoring units can be adjusted independently; and different from traditional integrated systems, distributed and mobile monitoring units are used, such that the monitoring units with different functions can be disposed at more suitable positions, and the reference value of monitoring data is improved.

Figure 1:
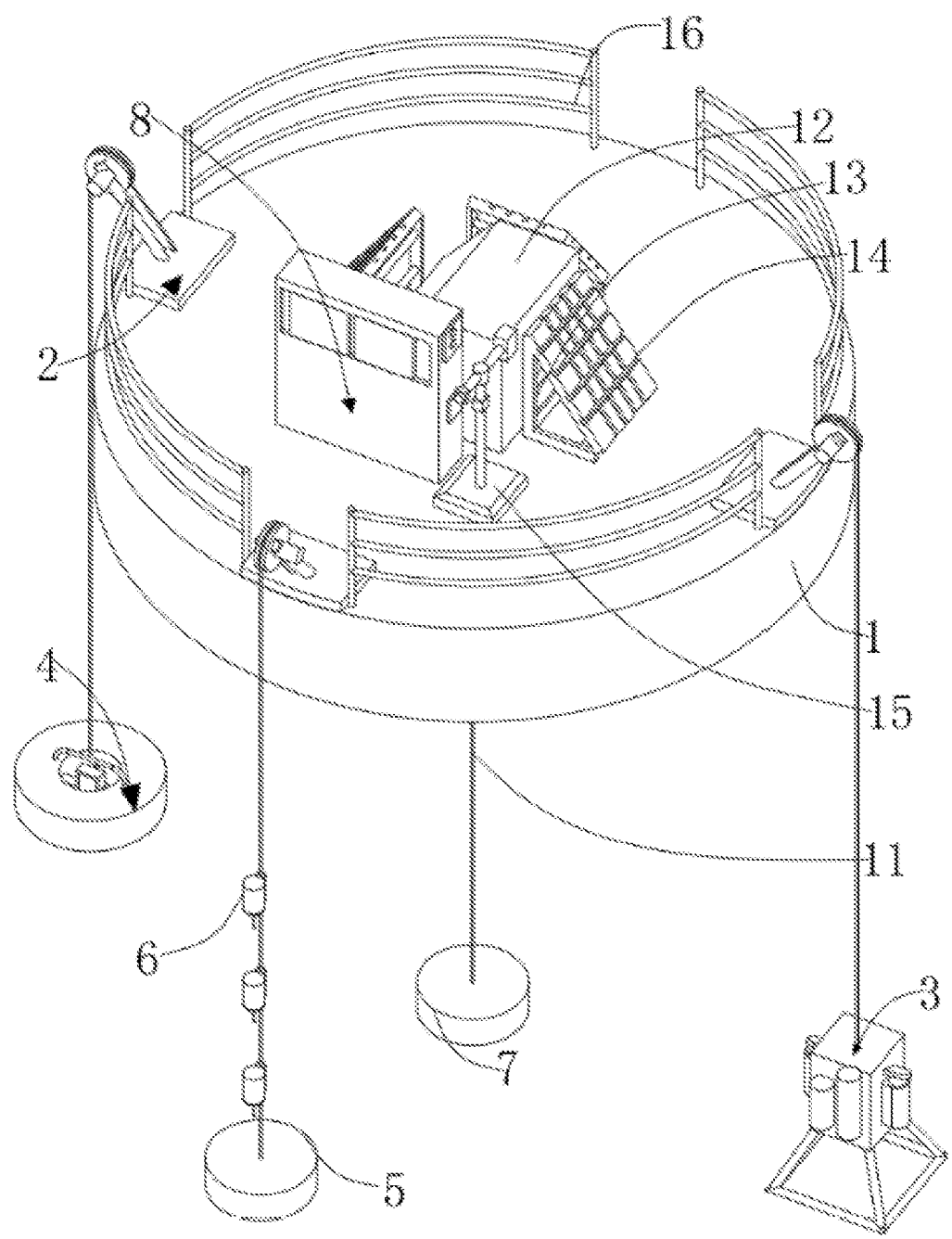
FIG. 1 is a structural view of a min part in Embodiment 1 and Embodiment 3 of the invention.
Figure 2:
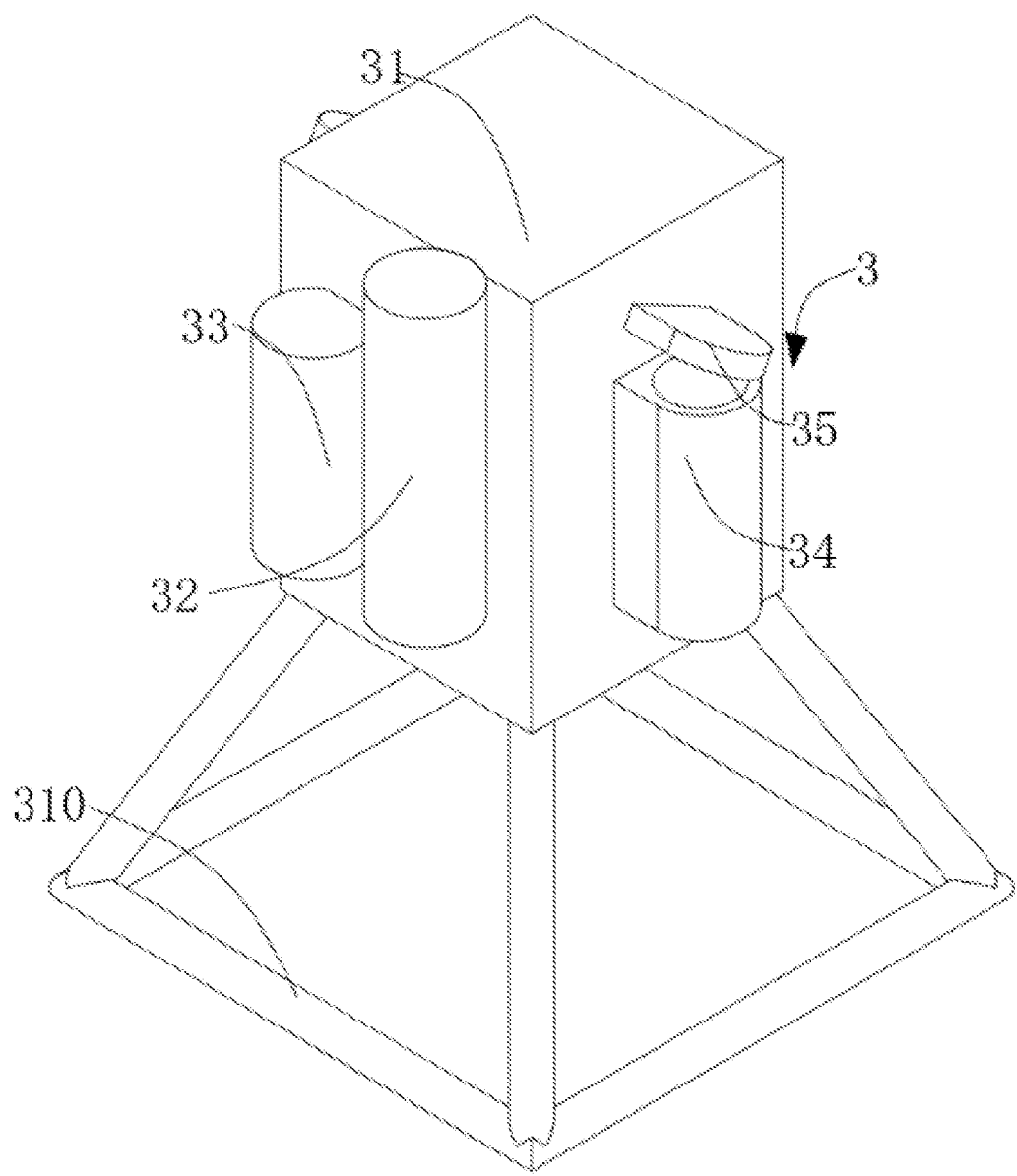
FIG. 2 is a structural view of a water quality monitoring assembly in Embodiment 1 and Embodiment 2 of the invention.
Figure 3:
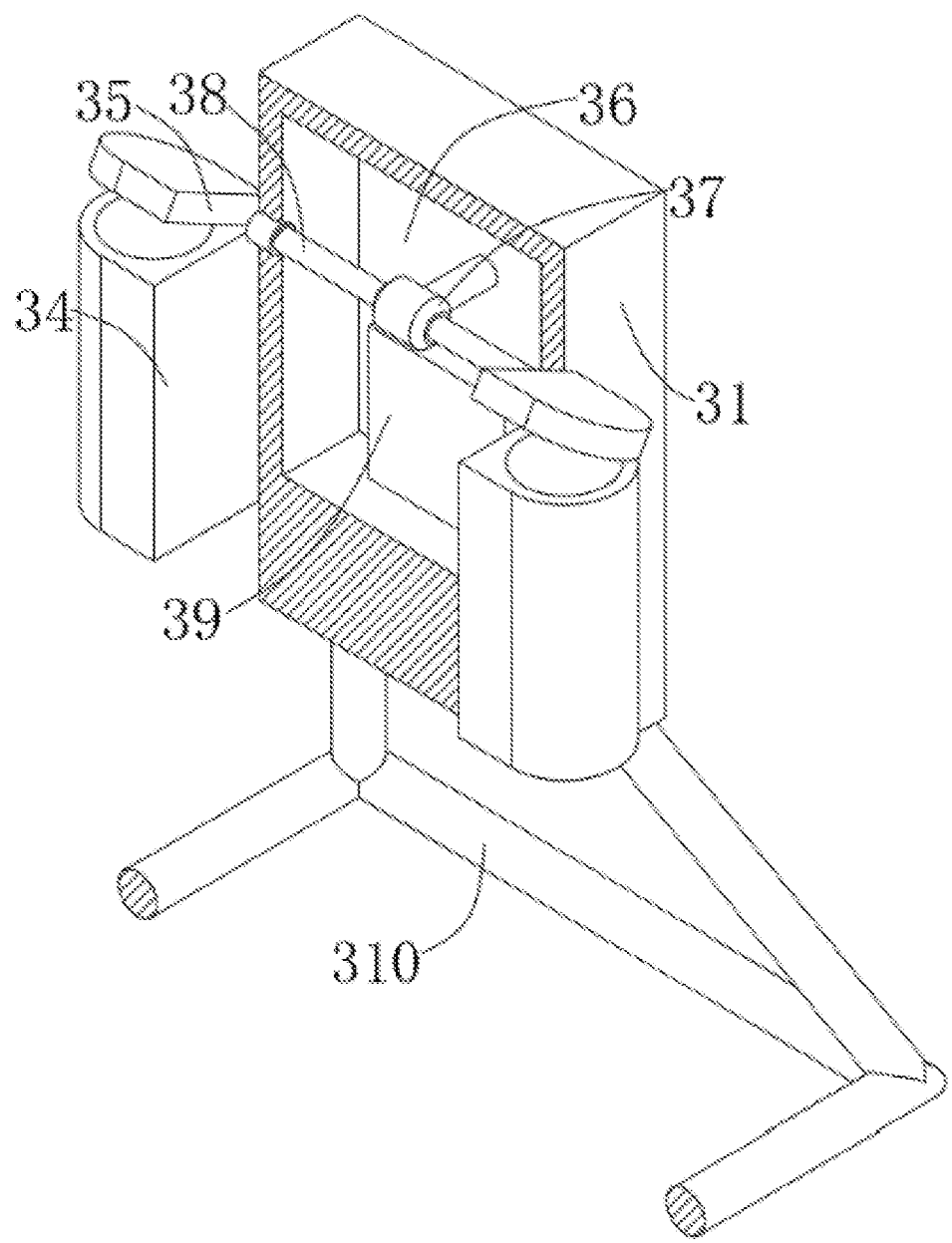
FIG. 3 is a sectional structural view of the water quality monitoring assembly in Embodiment 1 and Embodiment 2 of the invention.
Figure 4:
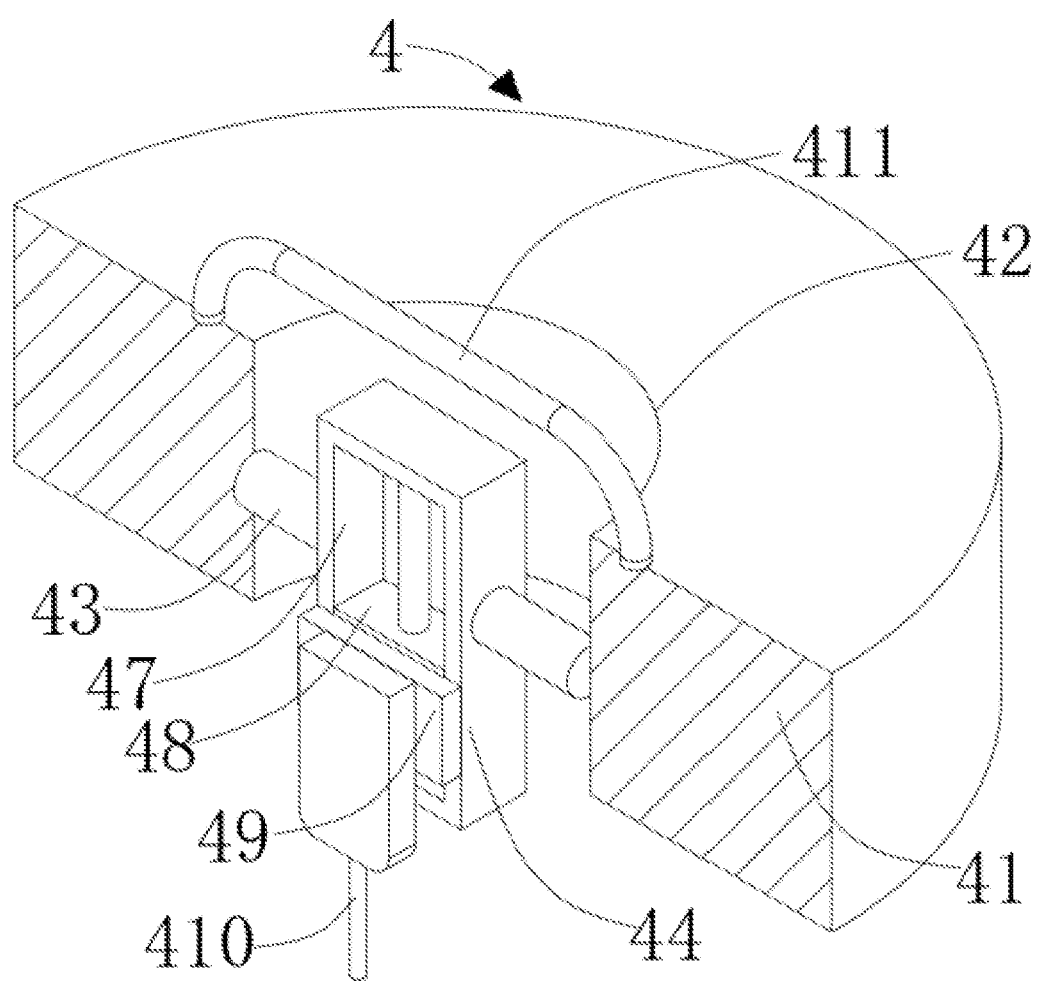
FIG. 4 is a sectional structural view of a sediment monitoring assembly in Embodiment 1 and Embodiment 2 of the invention.
Figure 5:
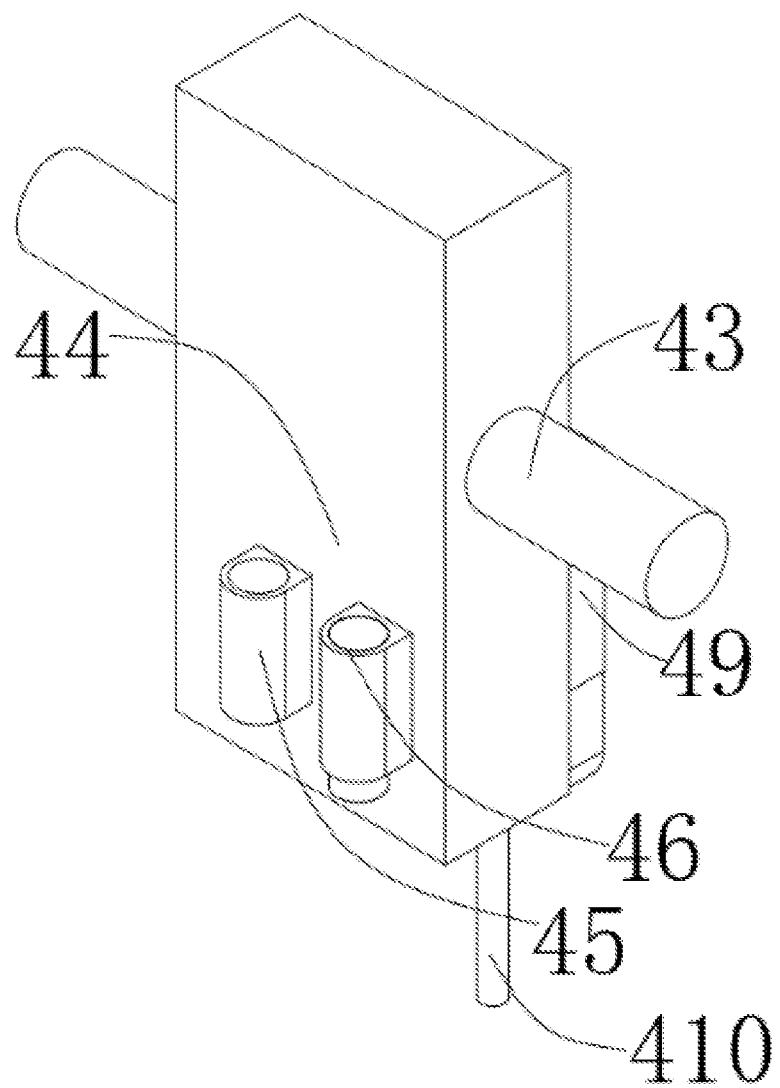
FIG. 5 is a structural view of a main plate in Embodiment 1 and Embodiment 2 of the invention.
Figure 6:
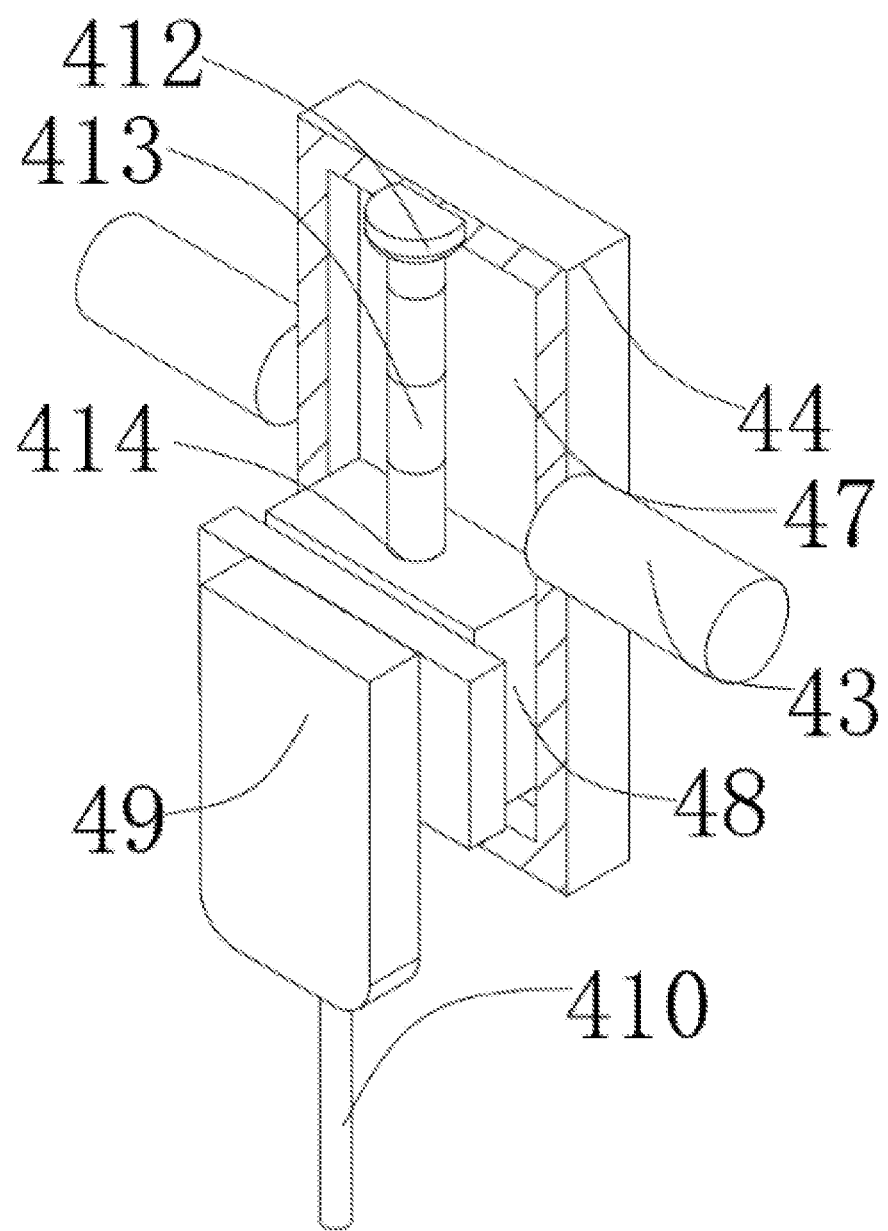
FIG. 6 is a sectional structural view of the main plate in Embodiment 2 of the invention.

In the figures: 1, floating platform; 2, take-up and pay-off assembly; 3, water quality monitoring assembly; 4, sediment monitoring assembly; 5, first balancing weight; 6, dissolved oxygen sensor; 7, second balancing weight; 8, central control unit; 11, second cable; 12, power distribution box; 13, oblique frame; 14, photovoltaic panel; 15, automatic meteorological station; 16, fence; 21, sheave wheel; 22, first cable; 23, base plate; 24, oblique rod; 25, first gear motor; 31, shell; 32, dissolved oxygen meter; 33, pressure sensor; 34, water quality sampler; 35, cover plate; 36, cavity; 37, double-shaft gear motor; 38, drive shaft; 39, lithium battery; 310, counterweight frame; 41, circular counterweight shell; 42, vertical opening; 43, horizontal support rod; 44, main plate; 45, camera; 46, lamp; 47, sliding groove; 48, sliding block; 49, movable plate; 410, dissolved oxygen probe; 411, support; 412, second gear motor; 413, lead screw; 414, threaded sleeve; 81, shell; 82, touch display screen; 83, host computer; 84, transmission module; 85, terminal plate; 86, control panel.

DETAILED DESCRIPTION OF THE INVENTION

The technical solutions of the embodiments of the invention will be clearly and completely described below in conjunction with the accompanying drawings of the embodiments of the invention. Obviously, the following embodiments are merely illustrative ones, and are not all possible ones of the invention. All other embodiments obtained by those ordinarily skilled in the art based on the following ones without creative labor should also fall within the protection scope of the invention.

Embodiment 1

Referring to FIG. 1-FIG. 5 and FIG. 8, the invention provides the following technical solution: a device for stratified in-situ monitoring of the water quality and dissolved oxygen of sediments in a tidal river network region comprises a floating platform 1, wherein three take-up and pay-off assemblies 2 are fixedly connected the edge of a top surface of the floating platform 1, each take-up and pay-off assembly 2 comprises a sheave wheel 21, a first cable 22, a base plate 23, two oblique rods 24 and a first gear motor 25, a water quality monitoring assembly 3, a sediment monitoring assembly 4 and a first balancing weight 5 are fixedly connected to bottom ends of the three first cables 22 on the three take-up and pay-off assemblies 2 respectively, and a central control unit 8 is fixedly connected to the top surface of the floating platform 1;

The water quality monitoring assembly 3 comprises a shell 31, a pressure sensor 33 and a dissolved oxygen meter 32 are fixedly connected to one side of the shell 31, two water quality samplers 34 are fixedly connected to two sides of the shell 31 respectively, top ends of the water quality samplers 34 are open, two cover plates 35 are rotatably connected to the two sides of the shell 31 respectively and are located above the two water quality samplers 34, the center of a top end of the shell 31 is fixedly connected to a bottom end of the corresponding first cable 22, and the water quality samplers 34 are used for water sampling;

The sediment monitoring assembly 4 comprises a circular counterweight shell 41, a vertical opening 42 is vertically formed in the circular counterweight shell 41, two horizontal support rods 43 are fixedly connected to an inner wall of the vertical opening 42, a main plate 44 is fixedly connected between the two horizontal support rods 43, a camera 45 and a lamp 46 are fixedly connected to one side of the main plate 44, a sliding groove 47 is formed in a side, away from the camera 45, of the main plate 44, a sliding block 48 is vertically and slidably connected into the sliding groove 47, a movable plate 49 is fixedly connected to a side, located outside the sliding groove 47, of the sliding block 48, a dissolved oxygen probe 410 is fixedly connected to a bottom end of the movable plate 49, data monitored by the dissolved oxygen probe 410 is transmitted to the central control unit 8 in real time, and the camera 45 and the lamp 46 are used for observing the underwater condition.

Embodiment 2

Refer to FIG. 2-FIG. 6 which illustrate Embodiment 2 of the invention. In Embodiment 2 which is based on the above embodiment, a cavity 36 is formed in the shell 31, a double-shaft gear motor 37 is vertically and fixedly connected into the cavity 36 and is located between the two cover plates 35, two shaft ends of the double-shaft gear motor 37 are fixedly connected to two drive shafts 38 respectively, ends of the two drive shafts 38 are fixedly connected to shaft ends of the two cover plates 35 respectively, and the double-shaft gear motor 37 drives the cover plates 35 to rotate to seal or open the water quality samplers 34; the water quality monitoring assembly 3 has an online mode and an offline mode; in the online mode, the double-shaft gear motor 37 is started by manually operating a control panel 86 on the central control unit 8 to open the water quality samplers 34 and then seal the water quality samplers 34 to complete sampling, and the dissolved oxygen meter 32 is started to monitor samples; in the offline mode, the pressure sensor 33 receives a pressure signal and compares the pressure signal with a preset pressure, when the pressure signal indicates that the actual pressure reaches the preset pressure, the water quality monitoring assembly 3 reaches a desired depth, at this moment, the double-shaft gear motor 37 is started to open the water quality samplers 34 and then seal the water quality samplers 34 to complete sampling, and the dissolved oxygen meter 32 is started at the same time to monitor samples.

A bottom surface of the shell 31 is fixedly connected to a counterweight frame 310, and a lithium battery 39 is fixedly connected into the cavity 36.

A lead screw 413 is vertically and fixedly connected into the sliding groove 47, a threaded sleeve 414 is vertically and fixedly connected into the sliding block 48, and the lead screw 413 is threadedly connected to the threaded sleeve 414.

A second gear motor 412 is fixedly connected to an inner top surface of the main plate 44, a shaft end of the second gear motor 412 is fixedly connected to an end of the lead screw 413, a top surface of the circular counterweight shell 41 is fixedly connected to a support 411, the support 411 is fixedly connected to a bottom end of the corresponding first cable 22, the second gear motor 412 drives the lead screw 413 to rotate to drive the sliding block 48 to move through the threaded sleeve 414, so as to make the dissolved oxygen probe 410 to move downwards to perform monitoring, and data monitored by the dissolved oxygen probe 410 is sent to the central control unit 8.

Three dissolved oxygen sensors 6 are fixedly connected to the first cable 22 fixedly connected to the first balancing weight 5, a data storage card and a battery are disposed in each dissolved oxygen sensor 6, a second cable 11 is fixedly connected to a bottom surface of the floating platform 1, and a second balancing weight 7 is fixedly connected to a bottom end of the second cable 11.

Embodiment 3

Figure 7:
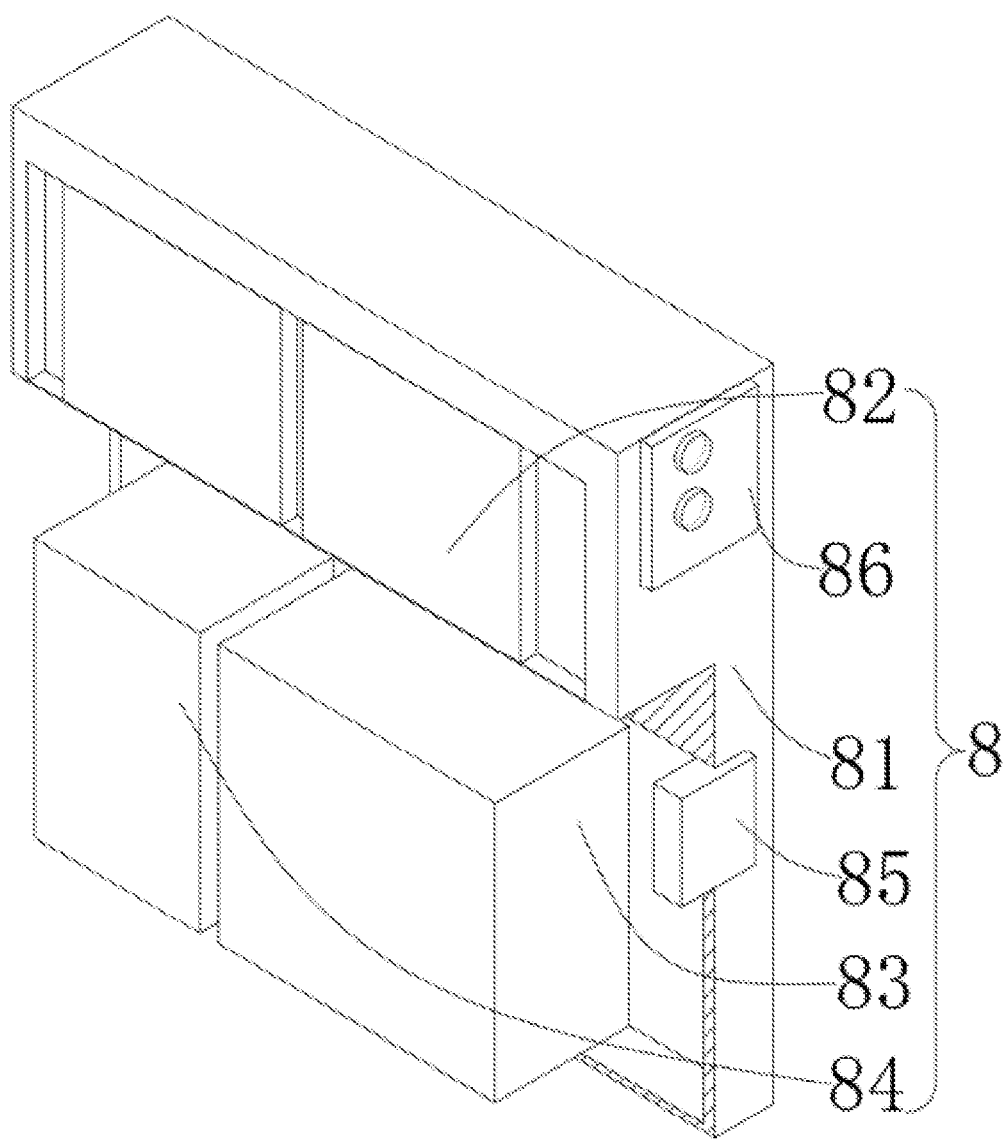
FIG. 7 is a sectional structural view of a central control unit in Embodiment 3 of the invention.
Figure 8:
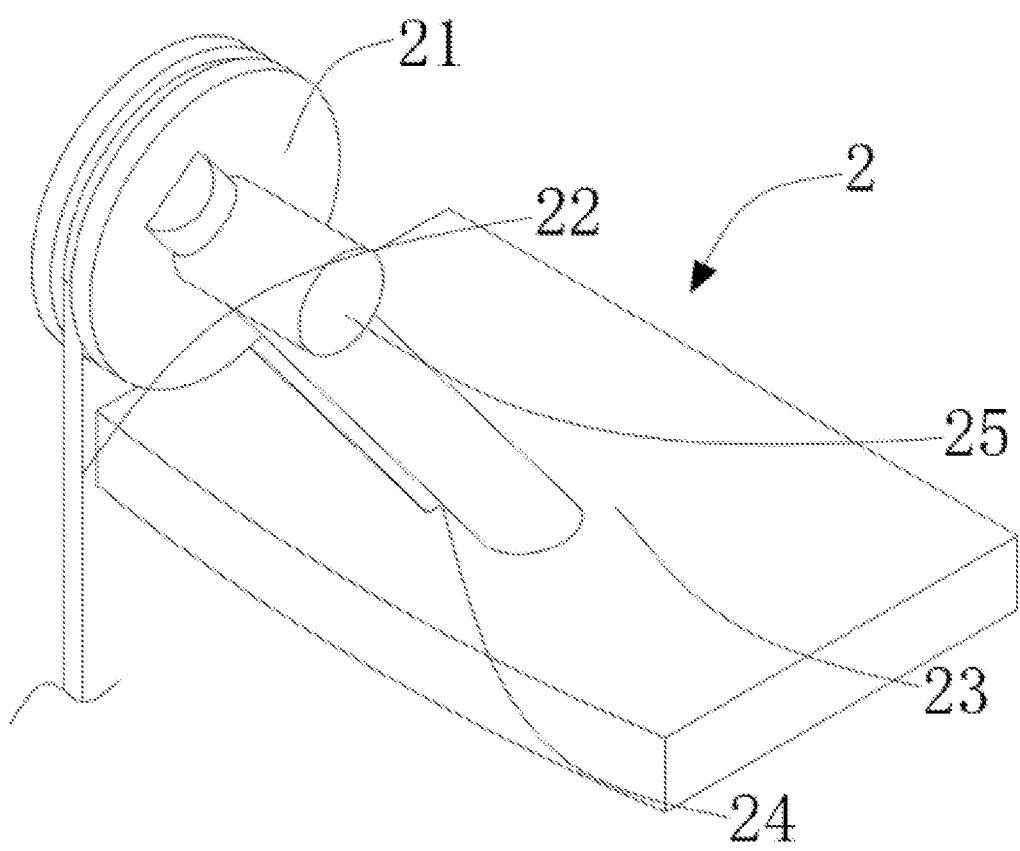
FIG. 8 is a structural view of a take-up and pay-off assembly in Embodiment 1 and Embodiment 3 of the invention.

Refer to FIG. 1 and FIG. 7-FIG. 8 which illustrate Embodiment 3 of the invention. In Embodiment 3 which is based on the above two embodiments, a power distribution box 12 is fixedly connected to the top surface of the floating platform 1, three oblique frames 13 are fixedly connected to the top surface of the floating platform 1 and are located around the power distribution box 12, photovoltaic panels 14 are fixedly connected to the oblique frames 13, an automatic meteorological station 15 is fixedly connected to the top surface of the floating platform 1 and is used for recording meteorological data such as wind speed, wind direction, air temperature, air humidity, air pressure and rainfall, and multiple fences 16 are fixedly connected to the edge of the top surface of the floating platform 1.

The base plates 23 are fixedly connected to the edge of the top surface of the floating platform 1 and are located between the multiple fences 16, the two oblique rods 24 are fixedly connected to a top surface of each base plate 23, the sheave wheel 21 is rotatably connected between top ends of the two oblique rods 24, the first cable 22 is wound on the sheave wheel 21, an end of the first cable 22 is fixedly connected to the sheave wheel 21, the first gear motor 25 is fixedly connected to one side of a top end of one of the two oblique rods 24, a shaft end of the first gear motor 25 is fixedly connected to an end of the sheave wheel 21, the first gear motor 25 is controlled by the central control unit 8, and the heights of monitoring components can be adjusted.

The central control unit 8 comprises a shell 81 fixedly connected to the top surface of the floating platform 1, a touch display screen 82 is fixedly connected to a side wall of a top surface of the shell 81, a host computer 83 and a transmission module 84 are fixedly connected into the shell 81, and a terminal plate 85 and a control panel 86 are fixedly connected to a side wall of the shell 81.

Embodiment 4

Refer to FIG. 1-FIG. 8 which illustrate Embodiment 4 of the invention, which is based on the above three embodiments. In this embodiment, when the device for stratified in-situ monitoring of the water quality and dissolved oxygen of sediments in a tidal river network region is used, meteorological data such as wind speed, wind direction, air temperature, air humidity, air pressure and rainfall is recorded in real time by the automatic meteorological station 15, water areas at different heights are monitored in real time by the multiple dissolved oxygen sensors 6, the water quality is sampled and monitored in real time by the water quality monitoring assembly 3, sediment data is monitored by the sediment monitoring assembly 4, these monitoring devices are mutually separated, and the positions of these monitoring devices can be adjusted automatically. The device can provide high-density data of stratified dissolved oxygen, all monitoring units perform sampling and monitoring directly at the positions where they are located, samples do not need to be transferred, sediments will not be disturbed, and monitoring is performed in the field environment, such that researchers can obtain the long-term diurnal change of stratified dissolved oxygen and the continuous change process of dissolved oxygen in one and even multiple hydrologic years, and basic data is provided for study of the dissolved oxygen change mechanism and accurate control of the water environment in tidal river network regions; during the monitoring process, the monitoring units are separated from each other, and the positions of the monitoring units can be adjusted independently; and different from traditional integrated systems, distributed and mobile monitoring units are used, such that the monitoring units with different functions can be disposed at more suitable positions, and the reference value of monitoring data is improved.

Although the embodiments of the invention have been illustrated and described above, those ordinarily skilled in the art should understand that various changes, amendments, substitutions and transformations can be made without departing from the principle and spirit of the invention. The scope of the invention should be defined by the claims and their equivalents.

What is claimed is:

1. A device for stratified in-situ monitoring of the water quality and dissolved oxygen of sediments in a tidal river network region, comprising a floating platform, wherein:
   three take-up and pay-off assemblies are fixedly connected to an edge of a top surface of the floating platform, each said take-up and pay-off assembly comprises a sheave wheel, a first cable, a base plate, two oblique rods and a first gear motor, a water quality monitoring assembly, a sediment monitoring assembly and a first balancing weight are fixedly connected to bottom ends of the three first cables on the three take-up and pay-off assemblies respectively, and a central control unit is fixedly connected to the top surface of the floating platform;
   the water quality monitoring assembly comprises a shell, a pressure sensor and a dissolved oxygen meter are fixedly connected to one side of the shell, two water quality samplers are fixedly connected to two sides of the shell respectively, top ends of the water quality samplers are open, two cover plates are rotatably connected to the two sides of the shell and are located above the two water quality samplers respectively, and a center of a top end of the shell is fixedly connected to a bottom end of the corresponding first cable;
   the sediment monitoring assembly comprises a circular counterweight shell a vertical opening is vertically formed in the circular counterweight shell, two horizontal support rods are fixedly connected to an inner wall of the vertical opening, a main plate is fixedly connected between the two horizontal support rods, a camera and a lamp are fixedly connected to one side of the main plate, a sliding groove is formed in a side, away from the camera, of the main plate, a sliding block is vertically and slidably connected into the sliding groove, a movable plate is fixedly connected to a side, located outside the sliding groove, of the sliding block, and a dissolved oxygen probe is fixedly connected to a bottom end of the movable plate.

2. The device for stratified in-situ monitoring of the water quality and dissolved oxygen of sediments in a tidal river network region according to claim 1, wherein a cavity is formed in the shell, a double-shaft gear motor is fixedly connected into the cavity and is located between the two cover plates, two drive shafts are fixedly connected to two shaft ends of the double-shaft gear motor respectively, and ends of the two drive shafts are fixedly connected to shaft ends of the two cover plates.

3. The device for stratified in-situ monitoring of the water quality and dissolved oxygen of sediments in a tidal river network region according to claim 2, wherein a counterweight frame is fixedly connected to a bottom surface of the shell, and a lithium battery is fixedly connected into the cavity.

4. The device for stratified in-situ monitoring of the water quality and dissolved oxygen of sediments in a tidal river network region according to claim 1, wherein a lead screw is vertically and rotatably connected into the sliding groove, a threaded sleeve is vertically and fixedly connected into the sliding block, and the lead screw is threadedly connected to the threaded sleeve.

5. The device for stratified in-situ monitoring of the water quality and dissolved oxygen of sediments in a tidal river network region according to claim 4, wherein a second gear motor is fixedly connected to an inner top surface of the main plate, a shaft end of the second gear motor is fixedly connected to an end of the lead screw, a top surface of the circular counterweight shell is fixedly connected to a support, and the support is fixedly connected to a bottom end of the corresponding first cable.

6. The device for stratified in-situ monitoring of the water quality and dissolved oxygen of sediments in a tidal river network region according to claim 4, wherein the base plates are fixedly connected to the edge of the top surface of the floating platform and are located between multiple fences, the two oblique rods are fixedly connected to a top surface of each said base plate, the sheave wheel is rotatably connected between top ends of the two oblique rods, the first cable is wound on the sheave wheel, an end of the first cable is fixedly connected to the sheave wheel, the first gear motor is fixedly connected to one side of a top end of one of the two oblique rods, and a shaft end of the first gear motor is fixedly connected to an end of the sheave wheel.

7. The device for stratified in-situ monitoring of the water quality and dissolved oxygen of sediments in a tidal river network region according to claim 1, wherein three dissolved oxygen sensors are fixedly connected to the first cable fixedly connected to the first balancing weight, a second cable is fixedly connected to a bottom surface of the floating platform, and a second balancing weight is fixedly connected to a bottom end of the second cable.

8. The device for stratified in-situ monitoring of the water quality and dissolved oxygen of sediments in a tidal river network region according to claim 1, wherein a power distribution box is fixedly connected to the top surface of the floating platform, three oblique frames are fixedly connected to the top surface of the floating platform and are located around the power distribution box, photovoltaic panels are fixedly connected to the oblique frames, an automatic meteorological station is fixedly connected to the top surface of the floating platform, and multiple fences are fixedly connected to the edge of the top surface of the floating platform.

9. The device for stratified in-situ monitoring of the water quality and dissolved oxygen of sediments in a tidal river network region according to claim 1, wherein the central control unit comprises a shell fixedly connected to the top surface of the floating platform, a touch display screen is fixedly connected to a side wall of a top surface of the shell, a host computer and a transmission module are fixedly connected into the shell, and a terminal plate and a control panel are fixedly connected to a side wall of the shell.

\* \* \* \* \*